US012752262B2

(12) United States Patent
Ong et al.

(10) Patent No.: US 12,752,262 B2
(45) Date of Patent: Oct. 6, 2026

(54) METHOD OF PRODUCING NANOSTRUCTURED IRON-BASED CATALYSTS FOR CONVERTING SYNGAS TO LIGHT OLEFINS

(71) Applicants: AGENCY FOR SCIENCE, TECHNOLOGY AND RESEARCH, Singapore (SG); IHI CORPORATION, Tokyo (JP)

(72) Inventors: Sze Wei Daniel Ong, Singapore (SG); Luwei Chen, Singapore (SG); Chee Kok Poh, Singapore (SG); Jie Chang, Singapore (SG); Noriki Mizukami, Tokyo (JP); Yoshinori Izumi, Tokyo (JP); Hiroyuki Kamata, Tokyo (JP); Armando Borgna, Singapore (SG)

(73) Assignees: AGENCY FOR SCIENCE, TECHNOLOGY AND RESEARCH, Singapore (SG); IHI CORPORATION, Tokyo (JP)

( * ) Notice: Subject to any disclaimer, the term of this patent is extended or adjusted under 35 U.S.C. 154(b) by 793 days.

(21) Appl. No.: 17/782,350

(22) PCT Filed: Dec. 3, 2020

(86) PCT No.: PCT/SG2020/050717
§ 371 (c)(1),
(2) Date: Jun. 3, 2022

(87) PCT Pub. No.: WO2021/112768
PCT Pub. Date: Jun. 10, 2021

(65) Prior Publication Data

US 2023/0032512 A1 Feb. 2, 2023

(30) Foreign Application Priority Data

Dec. 3, 2019 (SG) ............................ 10201911595T

(51) Int. Cl.
*B01J 21/08* (2006.01)
*B01J 23/00* (2006.01)
(Continued)

(52) U.S. Cl.
CPC ........... *B01J 23/8892* (2013.01); *B01J 21/08* (2013.01); *B01J 23/005* (2013.01); *B01J 23/78* (2013.01);
(Continued)

(58) Field of Classification Search
CPC ........ B01J 23/8892; B01J 35/23; B01J 21/08; B01J 23/005; B01J 23/78; B01J 37/035;
(Continued)

(56) References Cited

U.S. PATENT DOCUMENTS

| | | | | |
|---|---|---|---|---|
| 4,110,251 A * | 8/1978 | Lauder et al. | ........... | B01J 27/12 252/442 |
| 2013/0217569 A1* | 8/2013 | Ferdous et al. | .......... | B01J 23/78 502/245 |

(Continued)

FOREIGN PATENT DOCUMENTS

| | | | | |
|---|---|---|---|---|
| CN | 101396662 A | 4/2009 | | |
| WO | WO 2010/143783 A2 * | 12/2010 | .............. | B01J 23/74 |
| WO | WO-2014/024774 A1 | 2/2014 | | |

OTHER PUBLICATIONS

Top. Catal. 2003, 26, 55-71 (Xu et al.) (Year: 2003).*
(Continued)

*Primary Examiner* — Amy C Bonaparte
*Assistant Examiner* — Derek Rhoades
(74) *Attorney, Agent, or Firm* — MARSHALL, GERSTEIN & BORUN LLP

(57) ABSTRACT

The present invention relates to a method of preparing a nano-sized, iron-based catalyst, the method comprising: mixing a solution containing an iron salt with a surfactant to
(Continued)

form a mixture; adding a basic salt solution comprising a salt of element selected from the group consisting of: alkali metals, alkaline earth metals, transition metals of groups 3 to 7 and 9 to 11 of the Periodic Table of Elements, lanthanides, and combinations of elements thereof, to the mixture to form a precipitate; and calcining said precipitate to form the iron-based catalyst, said iron-based catalyst at least partially comprising said element of said basic salt. The present invention also relates to a nano-sized, iron-based catalyst prepared by the above method and a process for the production of light olefins using the nano-sized, iron-based catalyst.

14 Claims, 15 Drawing Sheets

(51) Int. Cl.

| | |
|---|---|
| ***B01J 23/78*** | (2006.01) |
| ***B01J 23/889*** | (2006.01) |
| ***B01J 35/30*** | (2024.01) |
| ***B01J 35/45*** | (2024.01) |
| ***B01J 35/70*** | (2024.01) |
| ***B01J 37/03*** | (2006.01) |
| ***B01J 37/04*** | (2006.01) |
| ***B01J 37/08*** | (2006.01) |
| ***C07C 1/12*** | (2006.01) |

(52) U.S. Cl.
CPC ............ *B01J 35/393* (2024.01); *B01J 35/45* (2024.01); *B01J 35/70* (2024.01); *B01J 37/035* (2013.01); *B01J 37/04* (2013.01); *B01J 37/088* (2013.01); *C07C 1/12* (2013.01); *B01J 2235/00* (2024.01); *B01J 2235/15* (2024.01); *B01J 2235/30* (2024.01); *C07C 2523/78* (2013.01)

(58) Field of Classification Search
CPC ........... B01J 37/04; B01J 37/088; C07C 1/12; C07C 2523/78
See application file for complete search history.

(56) References Cited

U.S. PATENT DOCUMENTS

2015/0225309 A1 8/2015 Tsubaki et al.
2016/0074849 A1 3/2016 Jiang et al.

OTHER PUBLICATIONS

CN 10139666 A (Zhang et al. English language machine translation) (Year: 2009).*
Russian Metallurgy 2014, 101-105 (Leushin et al.) (Year: 2014).*
Catalysts 2015, 5, 1352-1374 (Brunner et al.) (Year: 2015).*
Written Opinion in SG Application No. 11202250042P dated Mar. 13, 2024, 9 pages.
Bakavoli et al., Study on the carbon dioxide hydrogenation to hydrocarbons over nanoparticles iron-based catalyst, Petroleum & Coal, Dec. 31, 2014, vol. 56, No. 5, pp. 480-486.
Search Report and Written Opinion in International Application No. PCT/SG2020/050717 dated Feb. 18, 2021, 12 pages.
Xu et al., Synthesis of aromatics from syngas over FeMnK/Si02 and HZSM-5 tandem catalysts, Molecular Catalysis, Jun. 13, 2018, vol. 454, pp. 104-113.
Zhu et al., Enhancing the light olefin selectivity of an iron-based Fischer-Tropsch synthesis catalyst by modification with CTAB, RSC Advances, Sep. 14, 2018, vol. 8, No. 56, pp. 32073-32083.
Office Action in JP Application No. 2022-533069 dated Oct. 3, 2023, 10 pages.

* cited by examiner

METHOD OF PRODUCING NANOSTRUCTURED IRON-BASED CATALYSTS FOR CONVERTING SYNGAS TO LIGHT OLEFINS

CROSS-REFERENCE TO RELATED APPLICATIONS

This application claims the benefit of priority of Singapore patent application No. 10201911595T, filed on 3 Dec. 2019, its contents being hereby incorporated by reference in its entirety.

TECHNICAL FIELD

The present invention relates to methods of preparing nano-sized, iron-based catalysts capable of optimizing light olefins selectivity and yield.

BACKGROUND ART

Fischer-Tropsch synthesis may refer generically to a collection of chemical processes which use CO and $H_2$ as feedstock to produce longer-chain hydrocarbons. These processes usually take place over catalysts based on Co, Fe, Ru and even Ni and Re, and which are optionally supported over zeolites.

However, catalysts obtained via conventional processes were found to produce mainly paraffins and/or gasoline product fractions, with low yield for light olefins, e.g., $C_2$, $C_3$, and/or $C_4$ olefins.

Recent interest has re-surfaced on the use of Fe in the direct Fischer-Tropsch to olefin (FTO) process due to its lower cost compared to other materials. In particular, Fe-based catalysts promoted with elements of metals have shown various enhancements, such as active site dispersion, faster activation, suppression of methane and improvement to olefinicity of hydrocarbon products.

Typically, the incorporation of the metal(s) into the iron catalyst is usually done via incipient impregnation techniques, where the ratio of the metal element to Fe is relatively low, about 1:20 by weight. Further, an additional washing step may be needed to remove said metal cation.

Effective Fe-based catalysts for FTO require that the selectivity for light olefins be high and that for $CH_4$ to be low. However, known Fe-based catalysts have only been able to produce mainly paraffins and/or gasoline product fractions.

As such, there is a need to provide a catalyst and the preparation method thereof to overcome or at least ameliorate, one or more of the disadvantages described above. It is an object of the present disclosure to provide a one-pot synthesis method of iron-based catalysts effective for FTO.

SUMMARY OF INVENTION

In one aspect, there is provided a method of preparing a nano-sized, iron-based catalyst, the method comprising: i) mixing a solution containing an iron salt with a surfactant to form a mixture; ii) adding a basic salt solution comprising a salt of element selected from the group consisting of: alkali metals, alkaline earth metals, transition metals of groups 3 to 7 and 9 to 11 of the Periodic Table of Elements, lanthanides, and combinations of elements thereof, to the mixture to form a precipitate; and iii) calcining said precipitate to form the iron-based catalyst, said iron-based catalyst at least partially comprising said element of said basic salt.

The presently disclosed method may involve a one-pot co-precipitation procedure to form a nano-sized Fe catalyst using a basic salt solution. Advantageously, the co-precipitation method may enable a high amount (e.g., at least about 10% based on the total weight of catalyst) of the alkali metal, alkaline earth metal, transition metal of groups 3 to 7 or 9 to 11 of the Periodic Table of Elements, lanthanides, and combinations of elements thereof to be included or impregnated in the catalyst.

Without being bound to theory, the preparation of catalysts via such methods surprisingly yields nano-sized catalysts which adopt a unique iron-based spinel crystalline phase. This may be promoted by the metal in the basic salt solution.

Extended X-ray Absorption Fine structure (EXAFS) analysis of the nano-sized catalysts shows that the nano-sized catalysts form an iron-based phase which is neither $Fe_2O_3$ nor $Fe_3O_2$. It is postulated that the metal of the basic salt may be incorporated into the iron phase, leading to the unique spinel phase of the calcined catalyst. It is also postulated that the calcination step may facilitate the formation of said spiel crystalline phase. Advantageously, the spinel phase may assist the carburization step for the formation of $Fe_5C_2$.

Without being bound to theory, the high loading (e.g., at least about 10% based on the total weight of catalyst) of the promoter metals and the spinel crystalline phase in the catalyst may bring improvements on the catalyst performance. Advantageously, such iron based catalysts may provide enhanced catalytic activity for the conversion of carbon monoxide or carbon dioxide to light olefins via a Fischer Tropsch reaction. Advantageously, the conversion of carbon dioxide during the processes as described herein was found to be at least 50 mol C %.

Surprisingly, the current method may allow the precipitated catalyst to be calcined directly in air without washing, therefore reduce the impact to the environment as compared to the method of preparing said conventional fused/precipitated Fe catalyst.

Along with the improved conversion of the carbon monoxide or carbon dioxide gas, the catalyst obtained by the method may also demonstrate selectivity for light olefins comprising 2 to 4 carbon atoms over methane and long chain paraffins. Advantageously, the selectivity for methane during the processes as described herein was found to be less than 5% of the product gas stream.

In another aspect, there is provided a nano-sized, iron-based catalyst comprising: 5-99 wt. % of iron based on the total weight of the nano-sized catalyst; and 1-50 wt. % of an oxide of a metal selected from the group consisting of: alkali metals, alkaline earth metals, transition metals of groups 3 to 7 and 9 to 11 of the Periodic Table of Elements, and lanthanides, wherein said metal is not iron, wherein said nano-sized catalyst has a diameter of 2 to 50 nm. The catalyst may be prepared by the preparation methods disclosed herein.

In yet another aspect, there is provided a process for the production of light olefins, the process comprising the step of: i) heating the catalyst as described herein in the presence of a gas comprising one or more oxides of carbon and hydrogen to activate said catalyst; and ii) contacting said activated catalyst of step (i) with a gas stream comprising one or more oxides of carbon and hydrogen to partially or fully convert said one or more oxides of carbon to said light olefins, said light olefins comprising between 2 to 4 carbon atoms, wherein methane is substantially absent from said light olefins, or constitutes less than 20% of said light olefins.

Advantageously, the concentration of carbon monoxide in the product gas stream obtained from the process as disclosed herein was found to be less than 1%. Further advantageously, the yield of olefins of 2 to 4 carbons from the processes was found to be between 5-40%. The distribution of $C_2$ to $C_4$ hydrocarbons in the product gas was found to be at least 35%. In particular, it was found that at least 85 mol % of the product gas is olefins comprising 2 to 4 carbon atoms.

Definitions

The following words and terms used herein shall have the meaning indicated:

The term "promoted", in the context of the present disclosure, refers to the enhancement of catalytic activity or significant changes in the catalytic properties of a catalyst in the presence of an additional metal ion, preferably selected from the group consisting of alkali metals, alkaline earth metals, transition metals of groups 3 to 7 or 9 to 11 of the Periodic Table of Elements, or lanthanides, and combinations thereof. The words "promotion" and "promoter" should be construed accordingly.

The term "spinel crystalline phase", in the context of the present disclosure, refers to a class of minerals of general formulation $AB_2X_4$, which crystallise in the cubic (isometric) crystal system, with the X anions (typically chalcogens, like oxygen and sulfur) arranged in a cubic close-packed lattice and the cations A and B occupying some or all of the octahedral and tetrahedral sites in the lattice.

The term "light olefins", in the context of the present disclosure, refers to olefins or alkenes that comprise 2 to 4 carbon atoms. Light olefin may therefore refer to ethylene, propene and/or butene, whereby the butene may include but-1-ene, (22)-but-2-ene, (2E)-but-2-ene and 2-methylprop-1-ene.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. Exemplary, non-limiting embodiments of a carbonized composite for electrochemical cell electrodes, will now be disclosed.

The method of preparing a nano-sized iron-based catalyst as disclosed herein may comprise: mixing a solution containing an iron salt with a surfactant to form a mixture; adding a basic salt solution comprising a salt of element selected from the group consisting of: alkali metals, alkaline earth metals, transition metals of groups 3 to 7 and 9 to 11 of the Periodic Table of Elements, lanthanides, and combinations of elements thereof, to the mixture to form a precipitate; and calcining said precipitate to form the iron-based catalyst, said iron-based catalyst at least partially comprising said element of said basic salt.

The element may be selected from the group consisting of alkali metals, alkaline earth metals, transition metals of groups 3 to 7 or 9 to 11 of the Periodic Table of Elements, lanthanides, and combinations thereof. The alkali metal may be selected from the group consisting of lithium, sodium, potassium, rubidium, and caesium. The alkaline earth metal may be selected from the group consisting of beryllium, magnesium, calcium, strontium, and barium. The group 3 transition metal may be selected from the group consisting of scandium and yttrium. The group 4 transition metal may be selected from the group consisting of titanium, zirconium, and hafnium. The group 5 transition metal may be selected from the group consisting of vanadium, niobium and tantalum. The group 6 transition metal may be selected from the group consisting of chromium, molybdenum and tungsten. The group 7 transition metal may be selected from the group consisting of manganese, technetium and rhenium. The group 9 transition metal may be selected from the group consisting of cobalt, rhodium and iridium. The group 10 transition metal may be selected from the group consisting of nickel, palladium and platinum. The group 11 transition metal may be selected from the group consisting of copper, silver and gold. The lanthanide may be selected from the group consisting of lanthanum, cerium, praseodymium, neodymium, promethium, samarium, europium, gadolinium, terbium, dysprosium, holmium, erbium, thulium, ytterbium and lutetium.

In one embodiment, the basic salt comprises an alkali metal or an alkali earth metal. In a preferred embodiment, the basic salt comprises an alkali metal. In a more preferred embodiment, the basic salt comprises lithium, sodium, potassium, cesium, or combinations thereof. In a most preferred embodiment, the basic salt comprises sodium salts.

The basic salt may comprise hydroxide, carbonate or bicarbonate anions. In one embodiment, the basic salt comprises hydroxide anions. In a preferred embodiment, the basic salt comprises sodium hydroxide, lithium hydroxide, potassium hydroxide, cesium hydroxide, or combinations thereof.

Advantageously, the addition of the basic salt comprising a promoter metal may lead to the formation of the precipitate of the Fe-based catalyst, and may further enable the impregnation of the promoter metal into said Fe-based catalyst. Surprisingly, the catalyst obtained by said method was found to have a high loading (e.g., at least about 10% based on the total weight of catalyst) of the promoter metal, and adopt a spinel crystalline phase. Further advantageously, these properties were found to enhance the activity of the iron catalysts for the conversion of carbon monoxide or carbon dioxide to light olefins via a Fischer Tropsch reaction, and promote a good selectivity to light olefins over methane.

In one embodiment, the precipitated mixture obtained from step ii) is not washed before step iii). Advantageously, the precipitated mixture without washing step was found to have a high amount of the alkali metal promotor (e.g., at least about 10% based on the total weight of catalyst).

The adding step may comprise providing a molar ratio of elemental iron to the element of the basic salt of about from 1:2 to 1:25, preferably about 1:2 to 1:20, or about 1:2 to 1:18, or about 1:2 to 1:16, or about 1:2 to 1:15, or about 1:2 to 1:14, or about 1:2 to 1:13, or about 1:2 to 1:12, or about 1:2 to 1:11, or about 1:2 to 1:10, or about 1:3 to 1:10, more preferably about 1:4 to 1:10. In one embodiment, the molar ratio of elemental iron to the element of the basic salt is about 1:3.8.

The solution of step (i) may further comprise at least one or more additional salts of a transition metal, each independently selected from groups 3 to 7 and 9 to 11 of the Periodic Table of Elements. This may advantageously form a promoted Fe catalyst comprising an alkali metal and at least one additional transition metal.

The group 3 transition metal may be selected from the group consisting of scandium and yttrium. The group 4 transition metal may be selected from the group consisting of titanium, zirconium, and hafnium. The group 5 transition metal may be selected from the group consisting of vanadium, niobium and tantalum. The group 6 transition metal may be selected from the group consisting of chromium, molybdenum and tungsten. The group 7 transition metal may be selected from the group consisting of manganese, technetium and rhenium. The group 9 transition metal may be selected from the group consisting of cobalt, rhodium and iridium. The group 10 transition metal may be selected from the group consisting of nickel, palladium and platinum. The group 11 transition metal may be selected from the group consisting of copper, silver and gold.

In one embodiment, the transition metal is selected from group consisting of nickel, manganese, magnesium, calcium, lanthanum, cobalt, lithium, potassium, cerium, or a combination thereof. In a preferred embodiment, the transition metal is nickel or manganese. In a more preferred embodiment, the transition metal is manganese.

The transition metal salt may comprise an anion selected from the group consisting of hydroxide, carbonate, bicarbonate, nitrate, nitrite, chloride, fluoride, bromide, iodide, phosphate, pyrophosphate, perchlorate, and mixtures thereof. In one embodiment, the transition metal salt comprises nitrate anions.

In a preferred embodiment, the transition metal salt comprises $Mn(NO_3)_2$, $Ni(NO_3)_2$, or a combination thereof. In a more preferred embodiment, the transition metal salt comprises $Mn(NO_3)_2$. Without being bound to theory, by adding the transition metal salt, the transition metal may be introduced into the iron-based catalyst. Advantageously, the obtained catalyst may demonstrate improved selectivity for light olefins during FTO process.

The solution of step i) may comprise a molar ratio of elemental transition metal to iron of from about 1:5 to 1:200, preferably about 1:5 to 1:180, or about 1:5 to 1:160, or about 1:5 to 1:140, or about 1:5 to 1:120, or about 1:5 to 1:100, or about 1:8 to 1:100, or about 1:9 to 1:100, more preferably about 1:9 to 1:99.

In one embodiment, where the transition metal is nickel, the molar ratio of nickel to iron is about 1:50 to 1:200, or about 1:50 to 1:180, or about 1:50 to 1:160, or about 1:50 to 1:140, or about 1:50 to 1:120, or about 1:60 to 1:120, or about 1:70 to 1:120, or about 1:80 to 1:120, or about 1:90 to 1:110, more preferably about 1:100.

In another embodiment, where the transition metal is nickel, the molar ratio of manganese to iron is about 1:1 to 1:50, or about 1:1 to 1:40, or about 1:1 to 1:30, or about 1:1 to 1:20, or about 1:1 to 1:18, or about 1:1 to 1:16, or about 1:1 to 1:14, or about 1:1 to 1:12, or about 1:2 to 1:12, or about 1:3 to 1:12, or about 1:4 to 1:12, or about 1:5 to 1:12, or about 1:6 to 1:12, or about 1:8 to 1:12, or about 1:8 to 1:10, more preferably about 1:9.

The adding step ii) may further comprise introducing a silicate to the mixture and precipitating said Fe-based catalyst in the presence of the silicate to thereby form a silicate-supported Fe-based catalyst.

Without being bound to theory, a $SiO_2$ matrix may be formed by the hydrolysis of the silicate. Advantageously, said $SiO_2$ matrix may act as a promoter and improve the performance stability of the silicate-supported Fe-based catalyst.

The silicate may comprise one or more alkoxy groups of 2 to 15 carbon atoms, preferably 2-12 carbon atoms, 2-10 carbon atoms, or 2-8 carbon atoms, or 2-6 carbon atoms, or 2-5 carbon atoms. In one embodiment, the silicate is tetraethyl orthosilicate.

The adding step may comprise providing a molar ratio of elemental iron to said silicate of about 1:1 to 1:50, or about 1:1 to 1:45, or about 1:1 to 1:40, or about 1:1 to 1:35, or about 1:1 to 1:30, or about 1:1 to 1:25, or about 1:1 to 1:20, or about 1:1 to 1:18, or about 1:1 to 1:16, or about 1:1 to 1:15, or about 1:1 to 1:12, or about 1:2 to 1:12, more preferably about 1:5 to 1:12. In one embodiment, the molar ratio of elemental iron to said silicate is from 1:5 to 1:15. In a preferred embodiment, the molar ratio of elemental iron to said silicate is about 1:12.

The iron salt may be an iron (II) or iron (III) salt. In one embodiment, the iron salt is an iron (III) salt.

The iron salt may comprise an anion selected from the group consisting of nitrate, chloride, fluoride, bromide, iodide, phosphate, pyrophosphate and perchlorate. In one embodiment, the iron salt comprises nitrate anions.

In a preferred embodiment, the iron salt is iron (Ill) nitrate.

The surfactant may be an ionic surfactant. The surfactant may comprise an anion selected from the group consisting of: halides, sulfonates, sulfates, phosphates and carboxylates. In one embodiment, the surfactant comprises a halide anion.

In a preferred embodiment, the surfactant comprises fluoride, chloride, bromide or iodide anion. In a more preferred embodiment, the surfactant comprises a bromide anion.

Preferably, the surfactant may be a quaternary ammonium surfactant. More preferably, the surfactant may be cetrimonium bromide.

Without being bound to theory, the halogen anions present in the surfactant may also act as a promoter for the iron-based catalyst. It was found that the halogen anions had been shown to both suppress hydrogenation over Ni and may have an effect on enhancing olefin selectivity. It was also found that halogen anions reduce $Fe(CO)_5$ to $Fe_5C_2$ (i.e., the active carbide phase in FTO), and may play an important role during dynamic phase changes in Fe-based catalysts.

The molar ratio of iron to the surfactant may be about 1:0.5 to 1:15, or about 1:0.5 to 1:12, or about 1:0.5 to 1:10, or about 1:0.5 to 1:8, or about 1:0.5 to 1:6, or about 1:0.5 to 1:4, or about 1:0.5 to 1:2, or more preferably about 1:1.

Without being bound to theory, the ratio of iron to surfactant may affect the particle size of precipitated catalyst. The particle size may affect $CO/CO_2$ conversion, as well as the product selectivity. Advantageously, it was surprisingly found that the ratio of iron to surfactant as described herein may lead to a suitable particle size which achieves better selectivity towards desired products (i.e., light olefins).

The method as disclosed herein may further comprise collecting the precipitated nano-sized catalyst; and drying said precipitated nano-sized catalyst in air.

The collection of the precipitated nano-sized catalyst may be conducted by centrifugation and/or filtration.

The calcining step may be carried out at a temperature of about 300° C. to 600° C., or about 350° C. to 600° C., or about 400° C. to 600° C., or about 450° C. to 600° C., or about 500° C. to 600° C., or about 500° C. to 580° C., or about 500° C. to 560° C., or more preferably 500° C. to 550° C.

The calcining step may be carried out for about 1 to 10 hours, or about 1 to 8 hours, or about 1 to 6 hours, or about 1 to 5 hours, or about 1 to 4 hours, or about 1 to 3 hours, or about 1 to 2 hours, more preferably about 2 hours.

The mixture obtained from calcining step may be further washed. Advantageously, excess surfactant may be removed by the washing step. Without being bound to theory, high loading of surfactant (e.g., Br) may prevent oxidation of iron to iron oxide, which would affect $CO_2$ conversion process.

Advantageously, the nano-sized Fe catalysts obtained by the method as disclosed herein have shown to provide enhanced performance to light olefin selection, and when combined with a high catalytic activity, Fe-based FTO becomes commercially attractive as light olefin yield per pass is maximized.

Advantageously, nano-sized catalysts having the spinel crystalline phase may demonstrate improved conversion of carbon monoxide or carbon dioxide to light olefins, particularly light olefins comprising 2 to 4 carbon atoms, with up to 24 mol. C % improvement compared to conventional catalysts. The improved yields may be attributed to the crystalline spinel phase of the nano-sized catalysts.

In one embodiment, there is provided a method of producing a nano-sized Fe-based catalyst. The method begins by mixing iron nitrate and cetyl trimethyl ammonium bromide (CTAB) in deionized water. NaOH solution is used to precipitate the iron from the solution. The precipitate is then collected without washing and calcined in air at 550° C. for 2 h. This method produces Na-promoted nano-particles of about 4-5 nm in size in a single precipitation and calcination step without the need for any washing protocol to remove the Na cation and offers good performance in light olefin (C2-C4) selectivity and yield.

In another embodiment, the present invention provides a method of producing nano-sized Fe-based catalyst promoted with X, where X=Ni, Mn, Mg, Ca, La, Co, Li, K, Ce, or any of the combination thereof. The method begins by mixing iron nitrate, a salt of X and cetyl trimethyl ammonium bromide (CTAB) in deionized water. NaOH solution is used to precipitate the iron and X from the solution. The precipitate is then collected without washing and calcined in air at 500° C. or higher for at least 2 h. This method produces X-promoted nano-particles of about 4-5 nm in size in a single precipitation and calcination step without the need for any washing protocol to remove the X cation and offers good performance in light olefin (C2-C4) selectivity and yield.

In yet another embodiment, the present invention provides a method of producing supported nano-sized Fe-based catalyst, which may or may not be promoted with X, where X=Ni, Mn, Mg, Ca, La, Co, Li, K, Ce or any of the combination thereof.

The method begins by mixing iron nitrate, a salt of X if promotion with X is desired, and cetyl trimethyl ammonium bromide (CTAB) in deionized water. NaOH solution is used to precipitate the iron and X from the solution. Tetraethyl orthosilicate (TEOS) is added to form a silica matrix. The precipitate is then collected without washing and calcined in air at 500° C. or higher for at least 2 h. This method produces X-promoted nano-particles of about 4-5 nm in size in a single precipitation and calcination step without the need for any washing protocol to remove the Na cation and offers good performance in light olefin (C2-C4) selectivity, yield and enhanced stability.

The nano-sized, iron-based catalyst as disclosed herein may comprise: 5-99 wt. % of iron based on the total weight of the nano-sized catalyst; and 1-50 wt. % of an oxide of a metal selected from the group consisting of: alkali metals, alkaline earth metals, transition metals of groups 3 to 7 and 9 to 11 of the Periodic Table of Elements, and lanthanides, wherein said metal is not iron, wherein said nano-sized catalyst has a diameter of 2 to 50 nm.

Advantageously, the iron-based catalysts as described herein were found to demonstrate improved catalytic activity for the Fischer-Tropsch conversion of carbon monoxide or carbon dioxide to light olefins. In particular, the iron-based catalysts were found to demonstrate good selectivity for the light olefins over methane, as well as a higher overall conversion of the gas to light olefins.

Without being bound to theory, the improvement in catalytic activity may be attributed to the high amount of promoter metal, as well as the spinel crystalline phase of the iron-based catalysts. These properties of the catalyst may work synergistically to improve the performance of the catalysts.

The nano-sized catalyst may have a diameter in the range of about 2 nm to 50 nm, about 2 nm to about 5 nm, about 2 nm to about 10 nm, about 2 nm to about 20 nm, about 5 nm to about 10 nm, about 5 nm to about 20 nm, about 5 nm to about 50 nm, about 10 nm to about 20 nm, about 10 nm to about 50 nm, or about 20 nm to about 50 nm.

The metal may be present in an amount of 4-50 wt. % based on the total weight of the catalyst, or about 4-45 wt. %, or about 4-40 wt. %, or about 4-35 wt. %, or about 4-30 wt. %, or about 4-25 wt. %, or about 4-20 wt. %, or about 4-15 wt. %, or about 4-12 wt. %, or about 4-10.wt. %, more preferably about 10 wt. % based on the total weight of the catalyst.

Without being bound to theory, the catalyst may retain a high amount of the metals (~10 wt. %) in the catalyst as compared to the conventional loading amount.

Advantageously, retaining the metals at such a high amount as promoters would avoid the need for further waste water treatment (e.g., washing step) during industrial synthesis, and therefore play an important role in cost analysis of the FTO technology.

The nano-sized catalyst may adopt a spinel crystalline phase. The formula of the catalyst having a spinel crystalline phase may have the formula $FeM_2O_4$. The metal M may be an alkali metal. The metal M may be sodium.

The nano-sized catalyst may further comprise a transition metal selected from groups 3 to 7 or 9 to 11 of the Periodic Table of Elements. In one embodiment, the transition metal is selected from groups 7 or 10. In a preferred embodiment, the transition metal is nickel or manganese.

The weight ratio of the transition metal to iron in the nano-sized catalyst is about 1:5 to 1:200, preferably about 1:5 to 1:180, or about 1:5 to 1:160, or about 1:5 to 1:140, or about 1:5 to 1:120, or about 1:5 to 1:100 or about 1:9 to 1:100, more preferably about 1:9 to 1:99.

The nano-sized catalyst may further comprise an oxide of a halogen. In one embodiment, the halogen is bromine.

The oxide of the halogen may be present in an amount of about 0.1 to 50 wt. %, or about 0.1 to 45 wt. %, or about 0.1 to 40 wt. %, or about 0.1 to 35 wt. %, or about 0.1 to 30 wt. %, or about 0.1 to 25 wt. %, or about 0.1 to 20 wt % based on the weight of the catalyst.

The iron-based catalyst may exhibit an extended x-ray absorption fine structure analysis spectrum as shown in FIG. 4. The iron-based catalyst may exhibit an X-ray diffraction diagram as shown in FIG. 10.

The nano-sized catalyst may further comprise a $SiO_2$ matrix.

The nano-sized catalysts as defined herein may be prepared according to the methods as defined above.

The process for the production of light olefins as disclosed herein may comprise the steps of i) heating the catalyst as disclosed herein in the presence of a gas comprising one or more oxides of carbon and hydrogen to activate said catalyst; and ii) contacting said activated catalyst of step i) with a gas stream comprising one or more oxides of carbon and hydrogen to partially or fully convert said one or more oxides of carbon to said light olefins, said light olefins comprising between 2 to 4 carbon atoms, wherein methane is substantially absent from said light olefins, or constitutes less than 20% of said light olefins.

Advantageously, the process may facilitate the presently disclosed catalysts to achieve a high conversion (e.g., at least 50 mol C %) of oxides of carbon to hydrocarbons. Advantageously, the conversion of carbon dioxide via the process as described herein may be at least 20 mol C %, or at least 30 mol C %, or at least 40 mol C %, or at least 50 mol C %.

In particular, the catalysts disclosed herein favor the formation of short chain olefins over paraffins, particularly light olefins comprising 2 to 4 carbon atoms.

Such light olefins are also selectively formed over methane using the presently disclosed iron-zeolite catalysts. The high conversion and selectivity of the iron-zeolite catalysts in the disclosed process may be attributed to the spinel phase of the iron nanoparticles which are particularly active for the formation of light olefins from oxides of carbons.

The oxides of carbon may be carbon monoxide (CO) or carbon dioxide ($CO_2$). In one embodiment, the oxide of carbon in the gas stream of step ii) is substantially carbon dioxide.

The step i) may be carried out at a temperature of about 200° C.-350° C., or about 200° C.-340° C., or about 220° C.-300° C., or about 230° C.-300° C. or about 240° C.-300° C., or about 250° C.-300° C., or about 260° C.-300° C., or about 270° C.-300° C., or about 280° C.-300° C., more preferably about 290° C.

The step ii) may be carried out at a temperature of about 200° C.-450° C., or about 220° C.-450° C., or about 240° C.-450° C., or about 260° C.-450° C. or about 280° C.-450° C., or about 300° C.-450° C., or about 300° C.-420° C., or about 300° C.-400° C., or about 320° C.-400° C., or about 330° C.-400° C., more preferably about 330° C.-390° C.

The step i) may be carried out at a pressure of about 5-30 bar, or about 5-25 bar, or about 5-20 bar, or about 5-15 bar, or about 5-10 bar, more preferably about 10 bar.

The step ii) may be carried out at a pressure of about 5-50 bar, or about 5-45 bar, or about 5-40 bar, or about 5-35 bar, or about 5-30 bar, or about 5-25 bar, or about 10-25 bar, or about 15-25 bar, more preferably about 20 bar.

The space velocity of the gas stream in step ii) may be about 1500 ml/g·h to 5000 ml/g·h, or about 1500 ml/g·h to 4500 ml/g·h, or about 1500 ml/g·h to 4000 ml/g·h, or about 1500 ml/g·h to 3500 ml/g·h, or about 1500 ml/g·h to 3000 ml/g·h, or about 1500 ml/g·h to 2500 ml/g·h, or more preferably about 2000 ml/g·h to 2500 ml/g·h.

The molar ratio of hydrogen to the one or more oxides of carbon in the gas may be about 4:1 to 1:3, or about 3:1 to 1:3, or about 2:1 to 1:3, or about 2:1 to 1:2, more preferably about 1:1.

Advantageously, the yield of methane in the product stream obtained from the process as described herein may be less than 15%, or less than 10%, or preferably less than 5% of the product gas stream. In addition, the concentration of carbon monoxide in the product gas stream may be less than 12%, or less than 10%, or less than 8%, or less than 5%, or less than 1%.

Further advantageously, the yield of olefins having 2 to 4 carbon atoms in the product stream obtained from the process as described herein may be at least 5 mol %, or between 5-90%, or between 5-85%, or between 5-80%, or between 5-75%, or between 5-70%, or between 5-65%, or between 5-60%, or between 5-55%, or between 5-50%, or between 5-45%, or at least between 5-40%.

The distribution of $C_2$ to $C_4$ hydrocarbons in the product gas may be at least 20 mol %, or at least 25 mol %, or at least 30 mol %, or at least 35%. Of this, at least 75%, or at least 80%, or at least 85 mol % are olefins comprising 2 to 4 carbon atoms.

In one embodiment, the preparation method as described herein begins by mixing a salt of Fe, such as $Fe(NO_3)_3$, with a surfactant, such as cetyl trimethylammonium bromide (CTAB), in deionized $H_2O$ to form a well-mixed solution. An alkali base, such as NaOH, is subsequently used to precipitate the iron in the solution. The precipitate is collected via centrifugation and dried in air before calcination at 550° C. for 2 h. The Fe oxide catalyst is then activated in syngas at 10 bar and 290° C. for 24 h to obtain iron carbide. An induction protocol was observed by tracking the performance of the catalyst at 370° C. and 20 bar in flowing syngas with $H_2/CO=1$. Upon reaching a high activity (>90 C mol. % CO conversion), the temperature and/or H2/CO ratio is tuned to maximize light olefin yield.

In another embodiment, the method of producing nano-sized Fe-based catalysts is carried out by mixing a salt of Fe, such as $Fe(NO_3)_3$, and a promoter salt, such as $Mn(NO_3)_2$, with a surfactant, such as CTAB, in deionized $H_2O$ to form a well-mixed solution. An alkali base, such as NaOH, is subsequently used to precipitate the iron in the solution. The precipitate is collected via centrifugation and dried in air before calcination at 500° C. for 5 h. The Fe oxide catalyst is then activated in syngas at 10 bar and 290° C. for 24 h to obtain iron carbide. An induction protocol was observed by tracking the performance of the catalyst at 370° C. and 20 bar in flowing syngas with $H_2/CO=1$. Upon reaching a high activity (>90 C mol. % CO conversion), the temperature and/or $H_2/CO$ ratio ca be tuned to maximize light olefin yield.

In another embodiment, the preparation method as described herein begins by mixing a salt of Fe, such as $Fe(NO_3)_3$, with a surfactant, such as CTAB, in deionized $H_2O$ to form a well-mixed solution. An alkali base, such as NaOH, is subsequently used to precipitate the iron in the solution. A structural promoter, such as $SiO_2$, is introduced via the hydrolysis of tetraethyl orthosilicate (TEOS) in the precipitate suspension. The precipitate is collected via centrifugation and dried in air before calcination at 550° C. for 2 h. The Fe oxide catalyst is then activated in syngas at 10 bar and 290° C. for 24 h to obtain iron carbide. An induction protocol was observed by tracking the performance of the catalyst at 370° C. and 20 bar in flowing syngas with $H_2/CO=1$. Upon reaching a high activity (>90 C mol. % CO conversion), the temperature and/or $H_2/CO$ ratio can be tuned to maximize light olefin yield.

Advantageously, it was found that the nano-sized Fe-based catalysts show significant improvements over conventional fused-Fe catalysts. This may be attributed to its nano-particulate nature and the high alkali metal loading, in particular Na, to promote the product selectivity to light olefins. The use of suitable support material may also enable the maintaining of the nano-morphology and its high activity. In particular, the CO conversion obtained by the method as described herein using said catalysts was surprisingly found to reach >95 C mol. %. depending on the induction protocol.

Further advantageously, unprocessed syngas which typically consists of CO and $H_2$ in equal molar concentration may be converted directly by the nano-sized Fe catalyst as described herein, as the water-gas shift (WGS) reaction may act as an in-built feature to tune the $H_2/CO$ molar ratios. Therefore, the $H_2/CO$ ratio of the feedstock does not require an adjustment to a higher ratio, leading to a reduction of the operation cost.

BRIEF DESCRIPTION OF DRAWINGS

The accompanying figures, together with the description below are incorporated in and form part of the specification. These figures serve to illustrate various embodiments and to explain various principles and advantages in accordance with a present embodiment.

FIG. 1*a* shows a macro rod-like structure of the iron sodium catalyst while FIG. 1*b* is a close-up of the Fe nanoparticles. The macro structure is composed of smaller Fe nanoparticles of about 4-5 nm in size.

EXAMPLES

Figure 1:
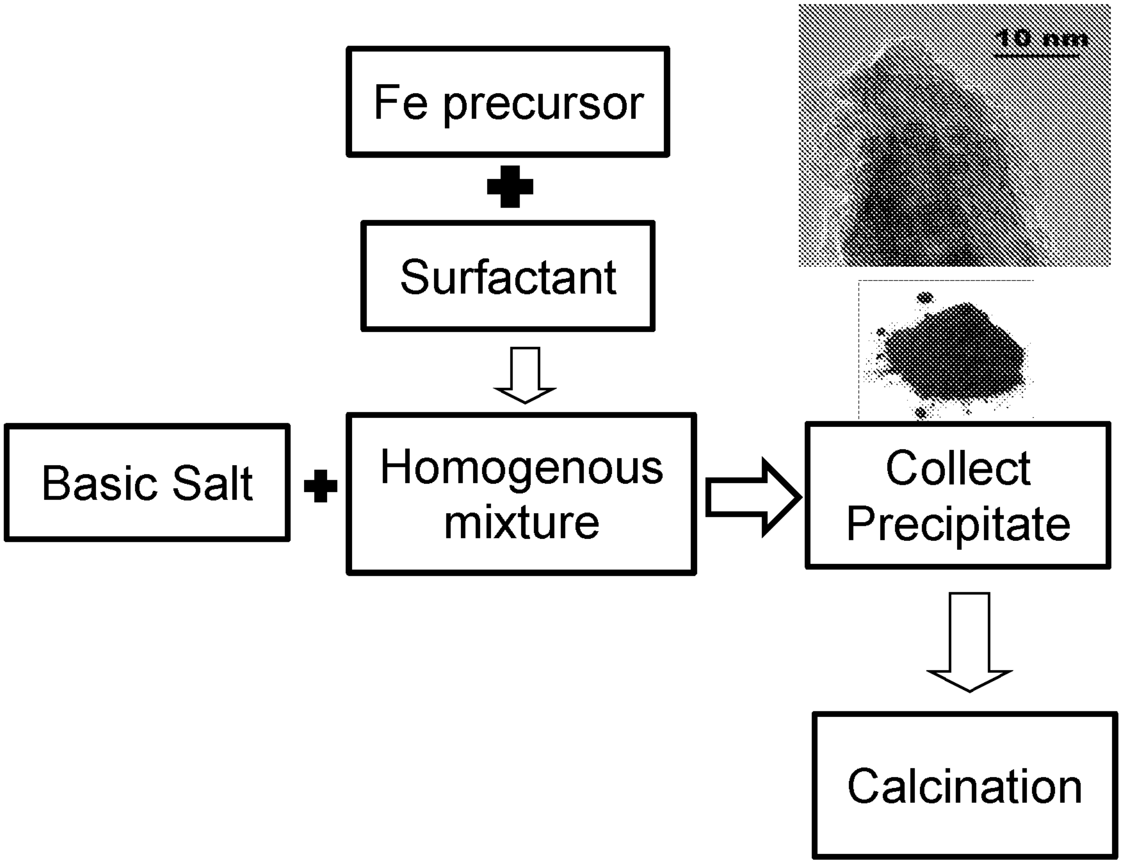
FIG. 1 is a flowchart illustrating the method of preparing the sodium-promoted nano-sized, iron based catalyst as described herein.

Non-limiting examples of the invention will be further described in greater detail by reference to specific Examples, which should not be construed as in any way limiting the scope of the invention.

Non-limiting examples of the invention will be further described in greater detail by reference to specific Examples, which should not be construed as in any way limiting the scope of the invention.

The following acronyms and symbols have the following meanings

GHSV: Gas hourly space velocity
TOS: Time on Stream
LO: Light Olefins
O: Olefins
P: Paraffin
CNT: Carbon Nanotubes
CNF: Carbon Nanofibres

Example 1—Preparation of Na-Promoted Fe Catalyst

Na-promoted Fe catalyst (FeNa) was prepared by mixing 10.81 g of $Fe(NO_3)_3 \cdot 9H_2O$ with 10 g cetyl trimethyl ammonium bromide (CTAB) in 400 ml deionized $H_2O$ to form a homogenous solution. 4 g of NaOH in 80 ml deionized $H_2O$ was subsequently used to precipitate the iron in the solution. The suspension was allowed to age at room temperature for 5 min. before collection of the precipitate via centrifugation. No washing of the precipitate was performed in order to allow the Na to remain as a promoter. The precipitate was then dried in air before calcination at 550° C. for 2 h. This yields a FeNa catalyst with a Na promotion of about 10 wt. %.

The FeNa catalyst was transferred to a fixed bed reactor and reduced in flowing $H_2$. A protocol flowing syngas in the ratio $H_2$/CO=1, 10 bar and 290° C. for 24 h was used to activate the catalyst. Finally, an induction period was observed by tracking the performance of the catalyst at 370° C. and 20 bar in flowing syngas with $H_2$/CO=1 at a space velocity of 2,000 ml/g·h. Upon reaching a high activity (>90 C mol. % CO conversion), the temperature and/or $H_2$/CO ratio may be tuned to maximize light olefin yield.

Figure 2A:
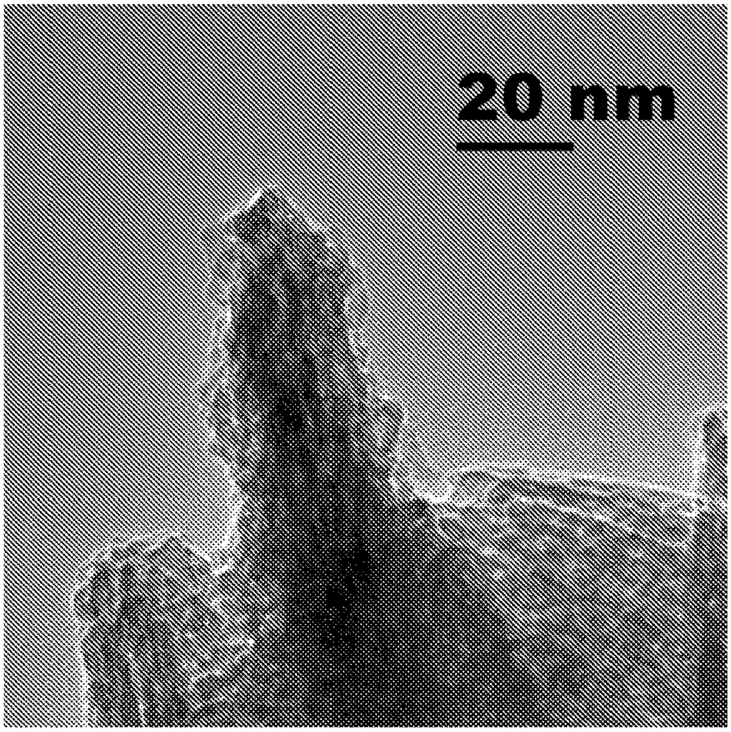
FIGS. 2*a* and 2*b* are transmission electron micrographs of the iron-sodium catalyst prepared by precipitation of $Fe(NO_3)_3$ with NaOH.
Figure 2B:
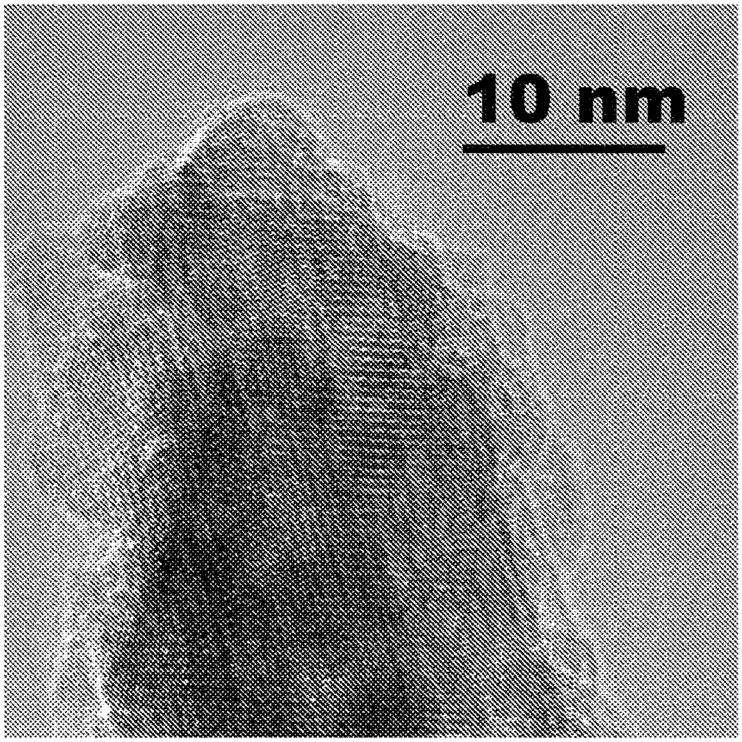
Figure 3:
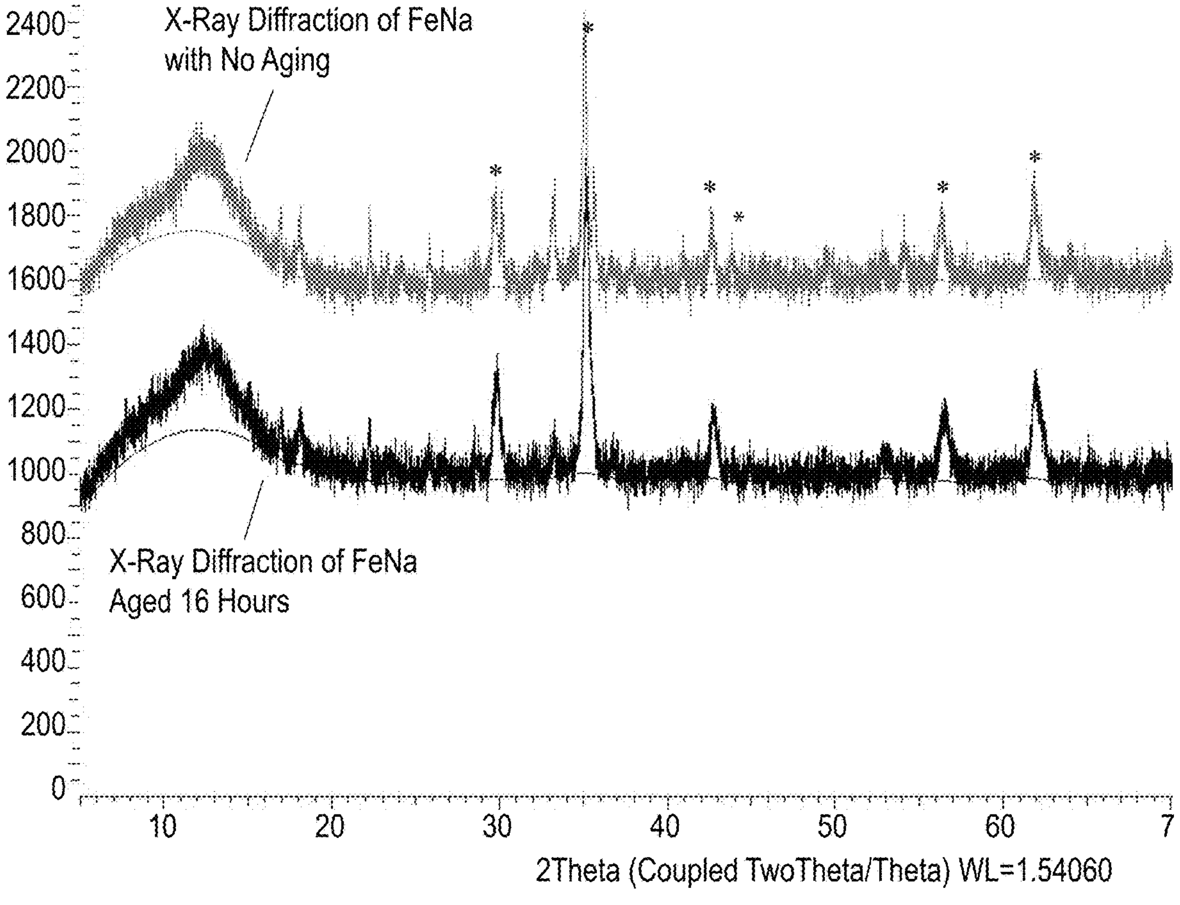
FIG. 3 shows the X-ray diffraction patterns of iron-sodium prepared through two methods. The peaks of the spinel phase of the FeNa catalyst are indicated by (*). The first method involved preparation of the catalyst at room temperature with no aging (top line) while the second method involved preparation of the catalyst at a temperature of 70° C. and left to age for 16 hours (bottom line). Catalysts prepared without aging (first method) exhibit peaks of both the spinel and hematite phases, indicating that the catalyst is formed with mixed hematite and spinel phases; while catalysts prepared with aging (second method) exhibit peaks of the spinel phase, indicating that the spinel phase is dominant. This demonstrates that it is possible to selectively form the spinel phase through preparation at higher temperature and aging.
Figure 4:
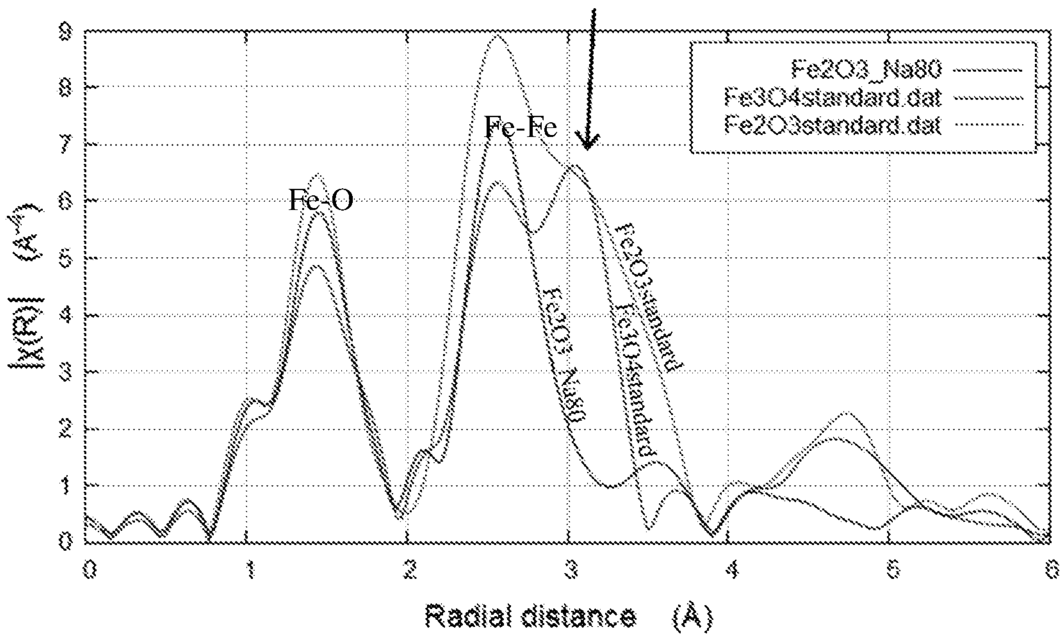
FIG. 4 is an extended X-ray absorption fine structure (EXAFS) spectrum of the iron-sodium catalyst. The spectrum of the FeNa catalyst prepared by methods described herein shows that the Fe—Fe coordination peak is lacking a shoulder typically seen in the spectra of $Fe_2O_3$ and $Fe_3O_4$, as indicated by the arrow. This implies that the phase of the FeNa spectrum is neither common hematite nor magnetite.
Figure 5A:
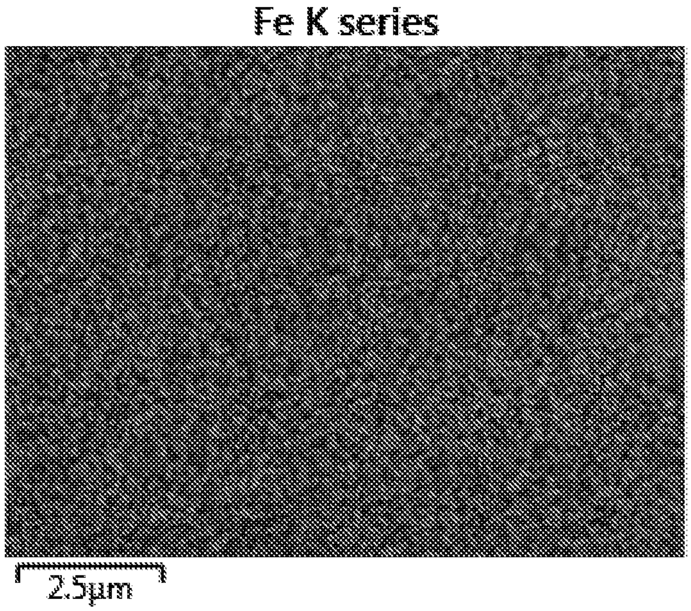
FIGS. 5*a*-5*d* are energy dispersive X-ray spectroscopy (EDS) map of the iron-sodium catalyst. The maps show a good dispersion of iron, bromine, sodium and oxygen. The EDS map of oxygen is also provided as a reference for the distribution of the elements.
Figure 5B:
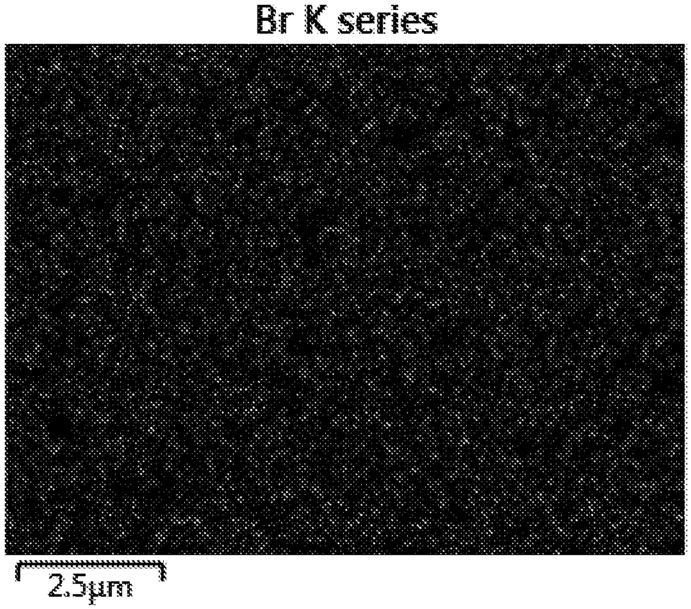
Figure 5C:
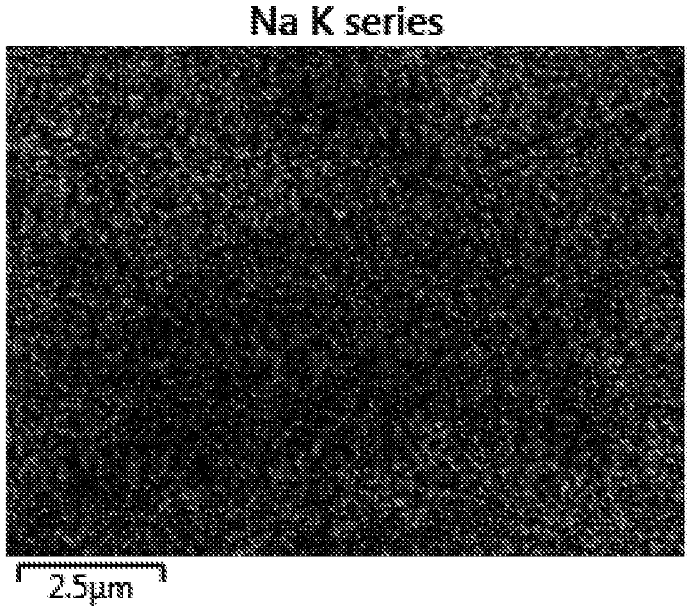
Figure 5D:
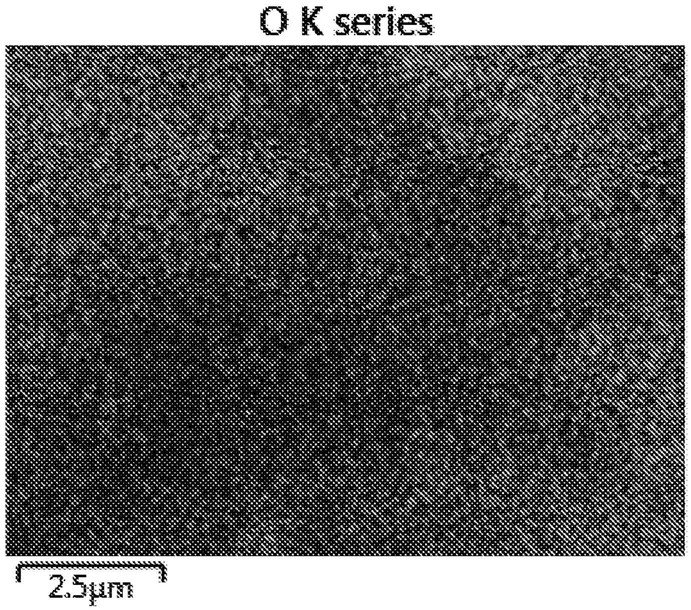

FIG. 2 shows the TEM images of the FeNa catalyst prepared herein, where the nanoparticles are clustered to form rod like features (FIG. 2*a*). Individual particles of the rod-like features can be seen in FIG. 2*b*. FIG. 3 shows the X-ray diffraction patterns of the FeNa catalyst. The major phase is a spinel phase that is based on iron. Follow-up studies with EXAFS indicate a phase with a missing Fe—Fe coordination peak when compared with spectra of $Fe_2O_3$ and $Fe_3O_4$, shown in FIG. 4. This suggests a formation of an iron-based phase that is neither common hematite nor magnetite.

Figure 6:
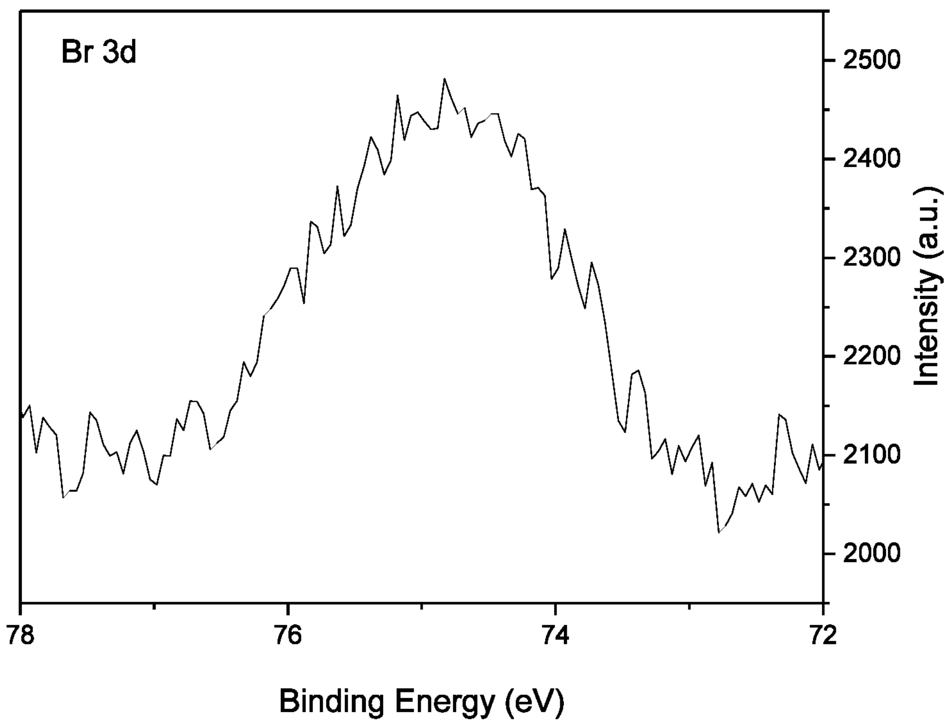
FIG. 6 is a X-ray photoelectron spectrum (XPS) of the peak corresponding to bromine in the iron-sodium catalyst. The binding energy of suggests that bromine is present in the form of the bromate ion is present.
Figure 7A:
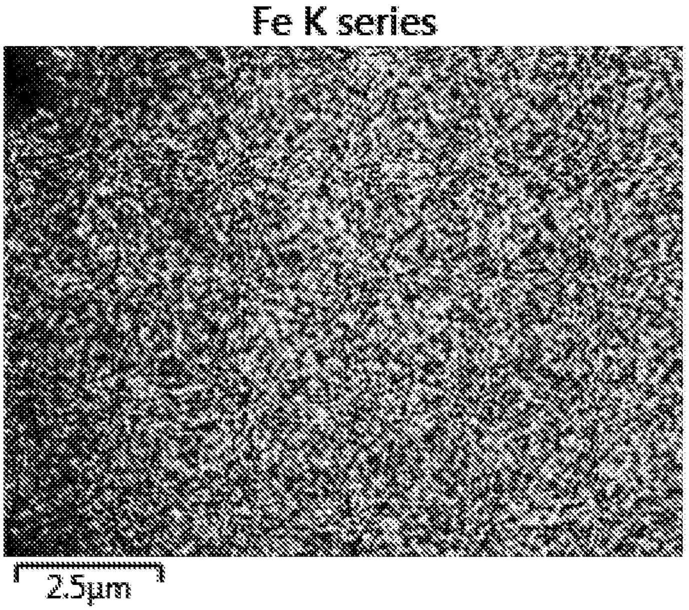
FIGS. 7*a*-7*e* are energy dispersive spectroscopy (EDS) maps of an iron-sodium-manganese catalyst showing the dispersion of iron, sodium and manganese. The map of oxygen is provided as a reference for the distribution of the elements.
Figure 7B:
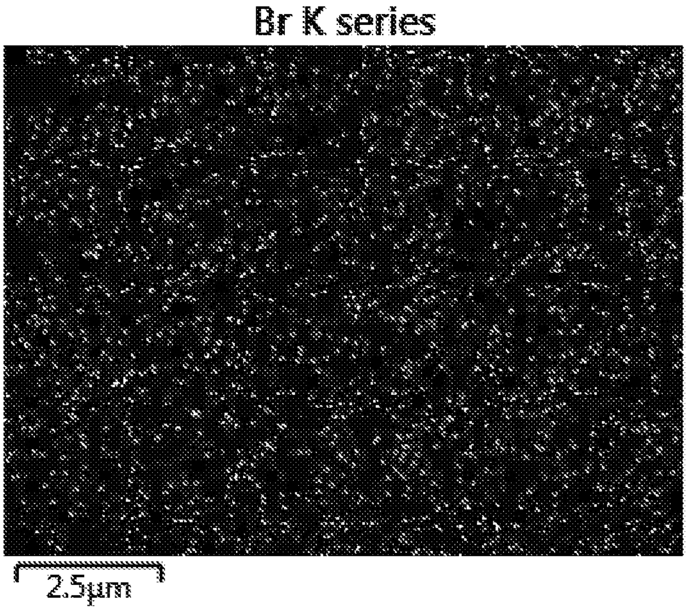
Figure 7C:
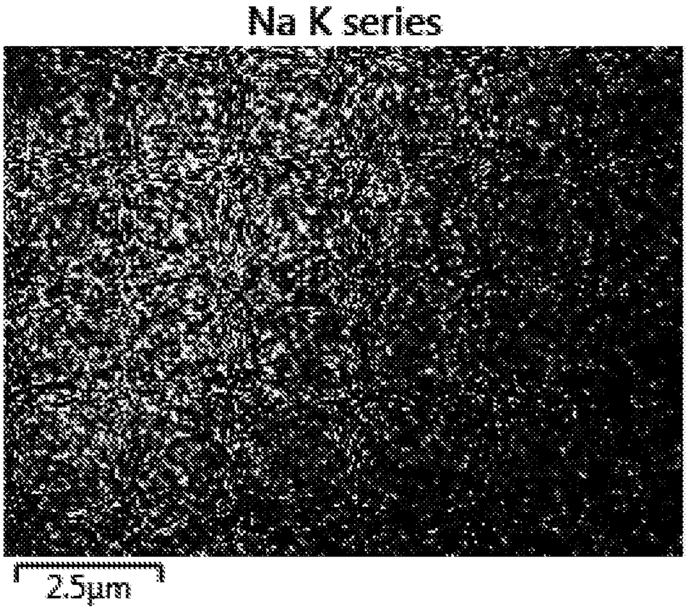
Figure 7D:
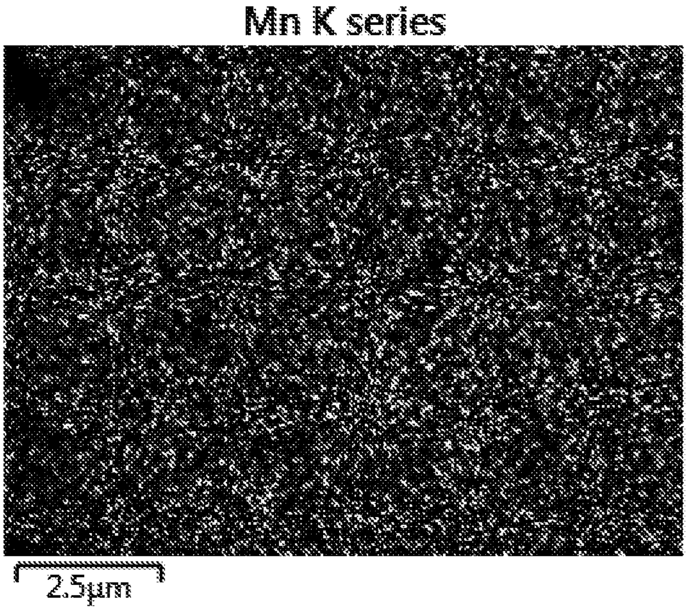
Figure 7E:
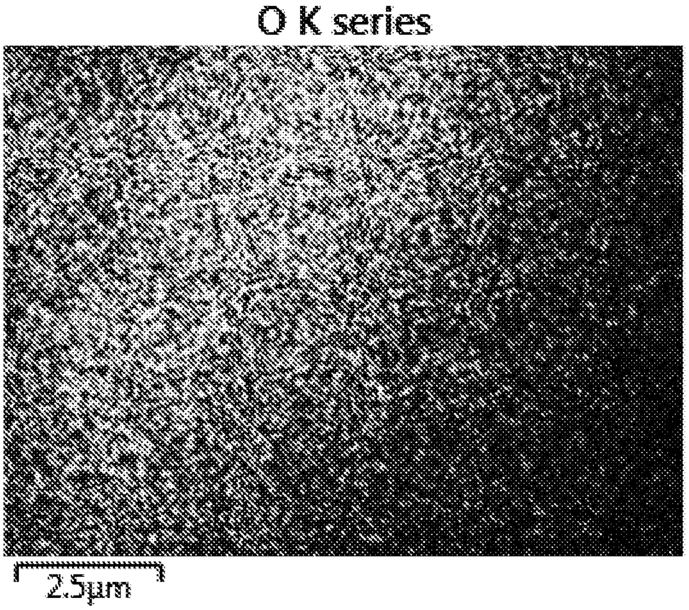
Figure 8A:
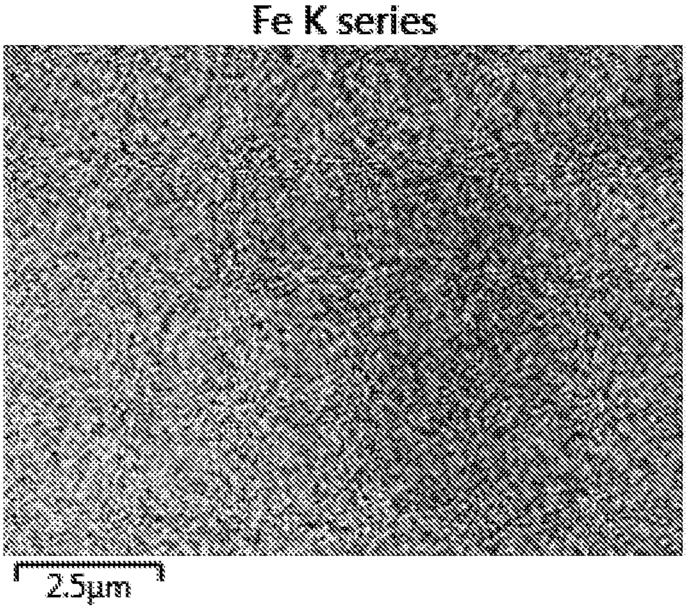
FIGS. 8*a*-8*e* are electron dispersive spectroscopy maps of an iron-sodium-nickel catalyst which shows the dispersion of iron, bromine, sodium and nickel. The map of oxygen is provided as a reference for the distribution of the elements.
Figure 8B:
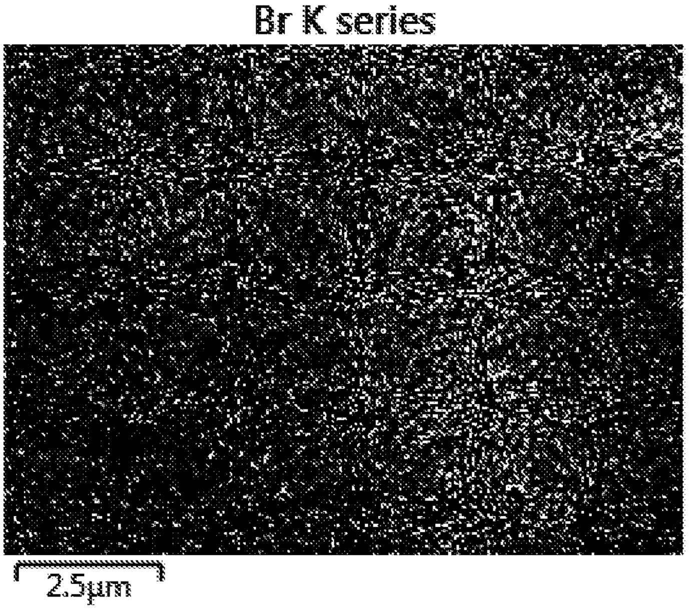
Figure 8C:
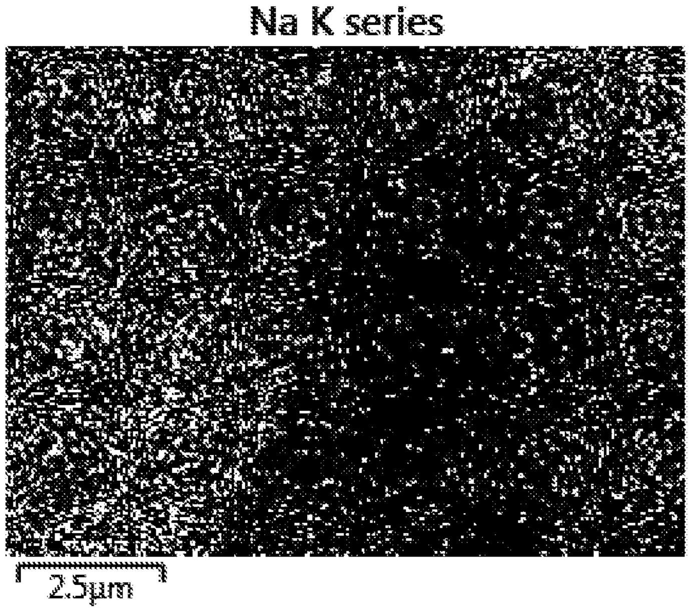
Figure 8D:
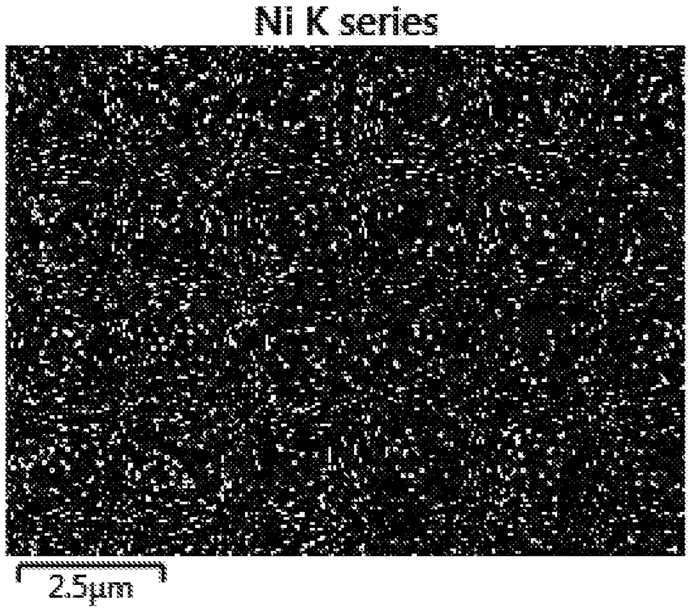
Figure 8E:
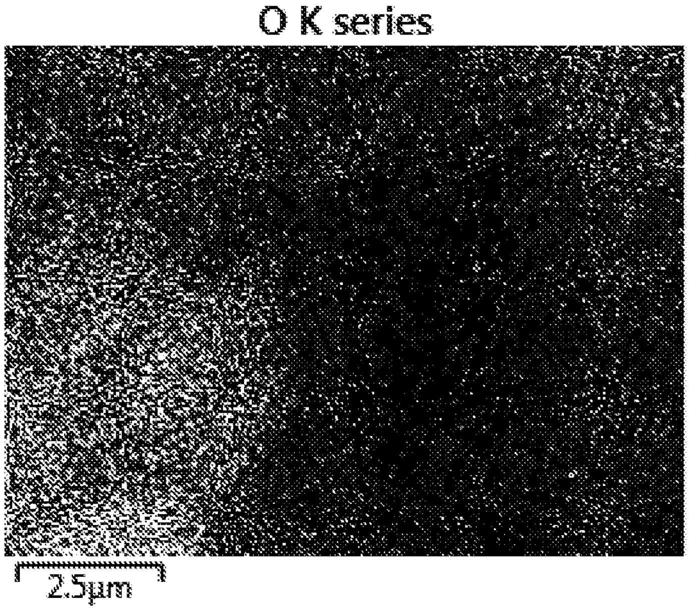

The composition of the FeNa catalyst was identified using EDS and the resulting color maps show a uniform dispersion of the elements in the catalyst, as shown in FIG. 5. FIG. 6 shows the XPS spectrum of FeNa for Br, where the binding energy suggests that Br is present in the catalyst in the bromate form and can be reduced to bromide during the reduction process in $H_2$. The reduced bromide form is believed to be able to facilitate $Fe_5C_2$ formation, when the catalyst is used in a Fischer-Tropsch reaction.

Table 1 shows the performance of FeNa during the induction period at 370° C., 20 bar, $H_2$/CO=1 and gas hourly space velocity (GHSV) of 2,000 ml/g·h. Data in Table 1 demonstrates that the catalyst allows low selectivity to $CH_4$ while allowing a high selectivity to $C_2$-$C_4$ light olefins. An optimal induction allows the catalyst to achieve high activity while maintaining a high selectivity to light olefins.

TABLE 1

Performance of FeNa, FeNa—Ni and FeNa—Mn during catalyst induction at 370 °C, 20 bar, $H_2$/CO = 1 and GHSV of 2,000 ml/g.h

| Catalyst | Conv. (C %) | $CH_4$ (C %) | $CO_2$ (C %) | Hydrocarbon Distribution (C %) | | | Light O/(O + P) (C %) | | | LO Yield (C %) |
|---|---|---|---|---|---|---|---|---|---|---|
| | | | | $CH_4$ | C2-C4 | C5+ | C2 | C3 | C4 | |
| FeNa | 58 | 7 | 45 | 18 | 47 | 35 | 67 | 90 | 84 | 12 |
| FeNa—Ni | 56 | 73 | 44 | 18 | 51 | 31 | 69 | 91 | 81 | 13 |
| FeNa—Mn | 59 | 6 | 44 | 17 | 51 | 32 | 71 | 92 | 86 | 14 |

Table 2 shows the performance of the FeNa catalyst at 350° C., 20 bar, $H_2$/CO=1 and GHSV of 2000 ml/g·h. The selectivity to $CH_4$ is minimized, while activity is maximized close to full CO conversion. A considerable fraction of $C_2$-$C_4$ is also obtained with high olefinicity. The FeNa catalyst allows olefin selectivity is also reasonably well-maintained to offer good light olefin yield per pass.

TABLE 2

Performance of the FeNa catalyst at 350° C., 20 bar, $H_2$/CO = 1 and GHSV of 2,000 ml/g.h.

| TOS (h) | Conv. (C %) | $CH_4$ (C %) | $CO_2$ (C %) | Hydrocarbon Distribution (C %) | | | Light O/(O + P) (C %) | | | LO Yield (C %) |
|---|---|---|---|---|---|---|---|---|---|---|
| | | | | $CH_4$ | C2-C4 | C5+ | C2 | C3 | C4 | |
| 64 | 97 | 5 | 40 | 15 | 48 | 37 | 58 | 89 | 84 | 22 |

Table 3 shows the performance comparison of the FeNa catalyst prepared by the described method (first row) with other reported catalysts with Na promotion (second to fourth row). The comparative catalysts were prepared by conventional impregnation of carbon-based supports with Fe catalysts with Na promotion followed by reduction in a $H_2$ environment before syngas reaction, without calcination. Comparisons are made with comparative catalysts which comprise the highest sodium promotion available. It can be seen that the FeNa catalyst prepared by the methods described herein exhibits high syngas conversion activity and olefinicity compared with other catalysts.

TABLE 3

Performance comparison of FeNa catalyst with other Na-promoted catalysts in the art.

| Catalyst | Conv.(C %) | $CO_2$ (C %) | Hydrocarbon Distribution (C %) $CH_4$ | C2-C4 | C5+ | Light O/(O + P) (C %) C2 | C3 | C4 | LO Yield (C %) |
|---|---|---|---|---|---|---|---|---|---|
| FeNa | 92 | 43 | 20 | 49 | 31 | 59 | 89 | 83 | 20 |
| Fe(Na + S)/CNF* | 98 | 53 | 10 | 60 | 30 | ← | 62 | → | 19 |
| Fe—24Na/CNT** | 71 | 14 | 7 | 22 | 72 | N.A. | 78 | N.A | 10 |
| Fe/CNT(0.5)*** | 51 | 38 | 4 | 20 | 76 | ← | 85 | → | 5 |

Example 2—Preparation of a Mn-Promoted FeNa Catalyst

Mn promoted FeNa (FeNa—Mn) catalyst was prepared by mixing 9.73 g of $Fe(NO_3)_3 \cdot 9H_2O$ and 0.67 g of $Mn(NO_3)_2 \cdot 4H_2O$ with 10 g CTAB in 400 ml deionized $H_2O$ to form a well-mixed solution. 4 g of NaOH in 80 ml deionized $H_2O$ was subsequently used to precipitate the iron in the solution. The suspension was allowed to age at room temperature for 5 min. before collection of the precipitate via centrifugation. No washing of the precipitate was performed in order to allow the Na to remain as a promoter. The precipitate was then dried in air before calcination at 550° C. for 2 h. This results in a FeNa—Mn catalyst with a Na promotion of about 10 wt. % and an Fe to Mn ratio of about 9.

The FeNa—Mn catalyst was transferred to a fixed bed reactor and reduced in flowing $H_2$. A protocol flowing syngas in the ratio $H_2/CO=1$, 10 bar and 290° C. for 24 h was used to activate the catalyst. Finally, an induction period was observed by tracking the performance of the catalyst at 370° C. and 20 bar in flowing syngas with $H_2/CO=1$ at a space velocity of 2,000 ml/g·h. Upon reaching a high activity (>90 C mol. % CO conversion), the temperature and/or $H_2/CO$ ratio may be tuned to maximize light olefin yield.

FIG. 7 show the EDS identification and mapping of the constituent elements in the FeNa—Mn catalyst. The images show a well dispersed and uniform distribution of Fe, Na and Mn, as well as the oxygen content present in oxide form. Table 1 shows the performance of FeNa—Mn when compared with FeNa. The Mn promotion decreases the selectivity to $CH_4$ and $C_5$+, while further improving the $C_2$-$C_4$ hydrocarbon selectivity and olefinicity.

Example 3—Preparation and Performance of Nickel-Promoted FeNa Catalyst

Ni promoted FeNa (FeNa—Ni) catalyst was prepared by mixing 10.70 g of $Fe(NO_3)_3 \cdot 9H_2O$ and 0.078 g $Ni(NO_3)_2 \cdot 6H_2O$ with 10 g CTAB in 400 ml deionized $H_2O$ to form a homogenous solution. 4 g of NaOH in 80 ml deionized $H_2O$ was subsequently used to precipitate the iron in the solution. The suspension was allowed to age at room temperature for 5 min. before collection of the precipitate via centrifugation. No washing of the precipitate was performed in order to allow the Na to remain as a promoter. The precipitate was then dried in air before calcination at 550° C. for 2 h. This results in a FeNa—Ni catalyst with a Na promotion of about 10 wt. % and an Fe to Ni ratio of about 99.

The FeNa—Ni catalyst was transferred to a fixed bed reactor and reduced in flowing $H_2$. A protocol flowing syngas in the ratio $H_2/CO=1$, 10 bar and 290° C. for 24 h was used to activate the catalyst. Finally, an induction period was observed by tracking the performance of the catalyst at 370° C. and 20 bar in flowing syngas with $H_2/CO=1$ at a space velocity of 2,000 ml/g·h. Upon reaching a high activity (>90 C mol. % CO conversion), the temperature and/or $H_2/CO$ ratio may be tuned to maximize light olefin yield.

FIG. 8 shows the EDS identification and mapping of the constituent atoms in the FeNa—Ni catalyst. The images show a well dispersed and uniform distribution of Fe, Na and Ni, as well as the oxygen content present in oxide form. Table 1 shows the reaction data of FeNa—Ni during induction at 370° C., 20 bar, $H_2/CO=1$ and GHSV of 2,000 ml/g·h. The addition of Ni is able to improve selectivity for the $C_2$-$C_4$ fraction at the expense of the $C_5$+ fraction due to its propensity to form very short chain hydrocarbons and is mainly active for the methanation of CO and $H_2$. This, combined with the olefinicity of the FeNa catalyst, is believed to allow a better selectivity for light olefins.

Example 4—Performance of FeNa Catalyst

A FeNa catalyst was prepared by mixing 10.81 g of $Fe(NO_3)_3 \cdot 9H_2O$ with 10 g CTAB in 400 ml deionized $H_2O$ to form a homogenous solution. 4 g of NaOH in 80 ml deionized $H_2O$ was subsequently used to precipitate the iron from the solution. The suspension was allowed to age at room temperature for 5 min. before collection of the precipitate via centrifugation. No washing of the precipitate was performed in order to allow the Na to remain as a promoter. The precipitate was then dried in air before calcination at 550° C. for 2 h. This results in a FeNa catalyst with a Na promotion of about 10 wt. %.

The FeNa catalyst was transferred to a fixed bed reactor and reduced in flowing $H_2$. A protocol flowing syngas in the ratio $H_2/CO=1$, 10 bar and 290° C. for 24 h was used to activate the catalyst. Finally, an induction period was observed by tracking the performance of the catalyst at 330° C. and 20 bar in flowing syngas with $H_2/CO=1$ at a space velocity of 12,000 ml/g·h. High activity of >78 C mol. % CO conversion can be achieved after 178 h, with no sign of deactivation.

Table 4 shows the performance of FeNa at 330° C., 20 bar, $H_2/CO=1$ and GHSV of 12,000 ml/g·h. Data in table 4 demonstrates that the catalyst becomes highly active, achieving about 80 C mol % CO conversion at high GHSV. The activity is maintained after 176 hours TOS.

TABLE 1

Performance of FeNa at 330° C., 20 bar, $H_2/CO$ = 1 and GHSV of 12,000 ml/g.h

| TOS | Conv. | $CH_4$ | $CO_2$ | Hydrocarbon Distribution (C %) | | | Light O/(O + P) (C %) | | | LO Yield |
|---|---|---|---|---|---|---|---|---|---|---|
| (h) | (C %) | (C %) | (C %) | $CH_4$ | C2-C4 | C5+ | C2 | C3 | C4 | (C %) |
| 176 | 78 | 10 | 37 | 18 | 41 | 41 | 39 | 82 | 58 | 14 |

Example 5—Supported FeNa Catalyst

The supported FeNa (s-FeNa) catalyst was prepared by mixing 1.08 g of $Fe(NO_3)_3 \cdot 9H_2O$ with 1 g of CTAB in 40 ml deionized $H_2O$ to form a well-mixed solution. 0.4 g of NaOH in 8 ml deionized $H_2O$ was subsequently used to precipitate the iron in the solution. The suspension was allowed to age at room temperature for 5 min., after which 7.14 ml of tetraethyl orthosilicate (TEOS) in 92.86 ml ethanol was introduced drop-wise to the suspension to create the $SiO_2$ support matrix. The final mixture was allowed to age for 12 h before collection of the precipitate via centrifugation. No washing of the precipitate was performed in order to allow the Na to remain as a promoter. The precipitate was then dried in air before calcination at 550° C. for 2 h. This results in an Fe-based catalyst with a Na promotion of about 1 wt. %.

Figure 9:
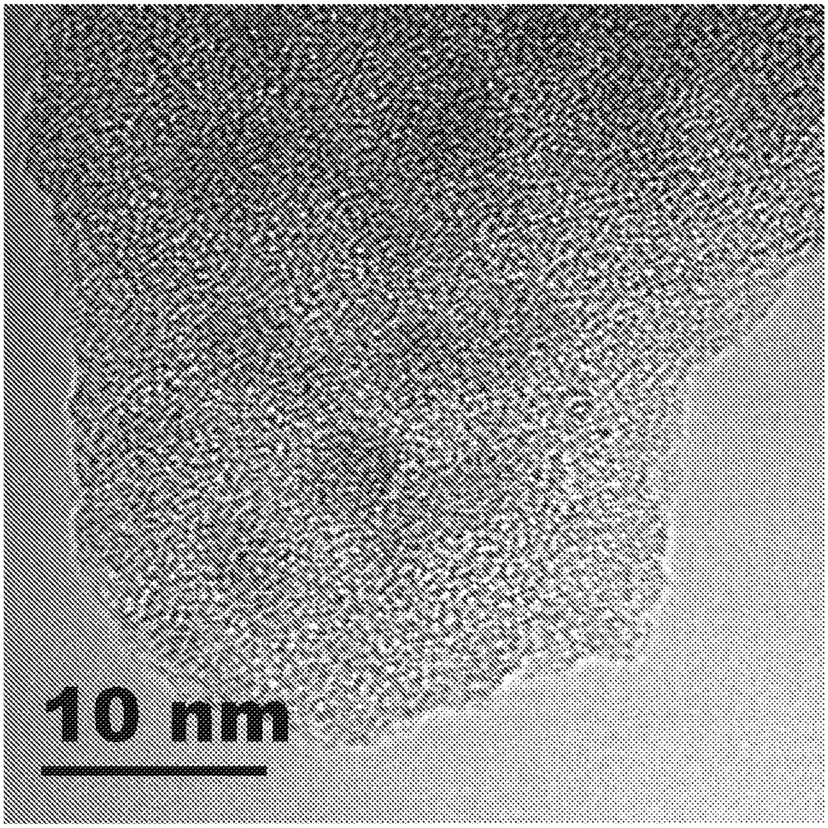
FIG. 9 is a transmission electron micrograph of an iron-sodium nanoparticle catalyst dispersed in a 90 wt. % silica matrix.
Figure 10:
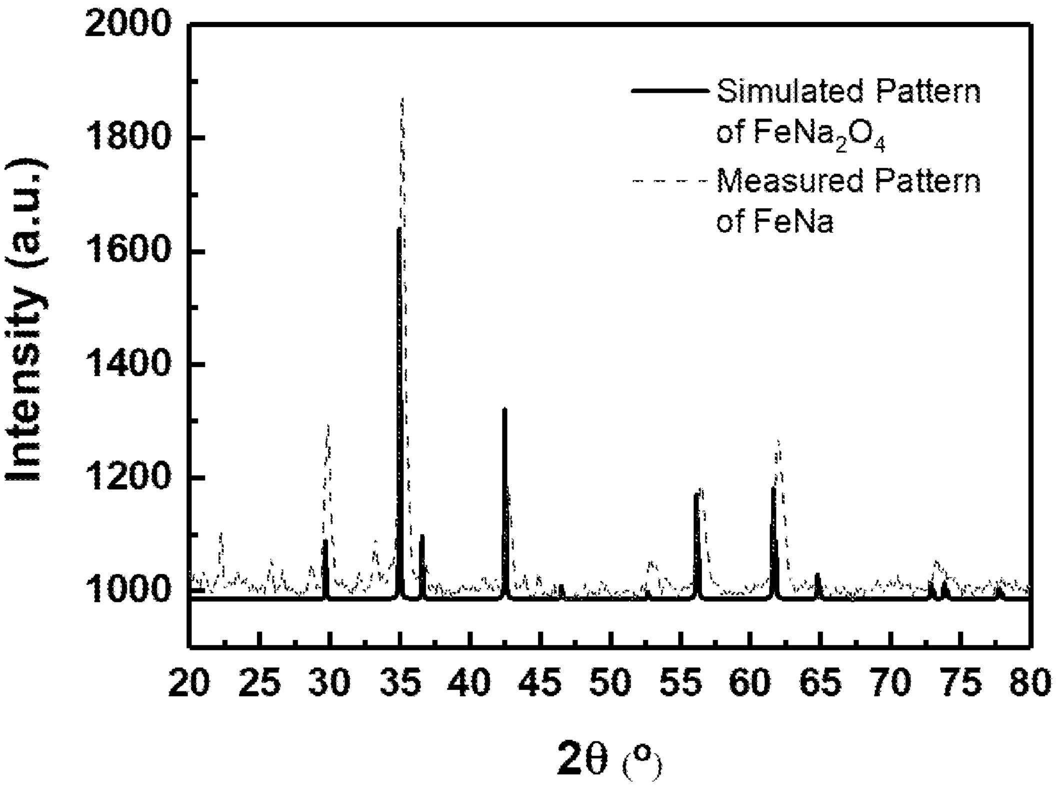
FIG. 10 shows the X-ray diffraction (XRD) diffraction patterns of FeNa in comparison to the simulated pattern of $FeNa_2O_4$.

The s-FeNa catalyst was transferred to a fixed bed reactor and reduced in flowing $H_2$. A protocol flowing syngas in the ratio $H_2/CO$=1, 10 bar and 290° C. for 24 h was used to activate the catalyst. Finally, an induction period was observed by tracking the performance of the catalyst at 330° C. and 20 bar in flowing syngas with $H_2/CO$=1 at a space velocity of 12,000 ml/g·h. High activity of >74 C mol. % CO conversion is achieved after 442 h, with no sign of deactivation. FIG. 9 shows the TEM of s-FeNa where the nanoparticles are dispersed throughout a $SiO_2$ matrix. The matrix stabilizes the nanoparticles, resisting particulate migration and sintering. Table 5 shows the performance of s-FeNa at 330° C., 20 bar, $H_2/CO$=1 and GHSV of 12,000 ml/g·h. The inclusion of the $SiO_2$ support activity of the catalyst can be stable past 442 h while operating at 74 C mol. %, allowing a consistent yield of light olefins.

TABLE 5

Performance of s-FeNa at 330 °C, 20 bar, $H_2/CO$ = 1 and GHSV of 12,000 ml/g.h.

| TOS | Conv. | $CH_4$ | $CO_2$ | Hydrocarbon Distribution (C %) | | | Light O/(O + P) (C %) | | | LO Yield |
|---|---|---|---|---|---|---|---|---|---|---|
| (h) | (C %) | (C %) | (C %) | $CH_4$ | C2-C4 | C5+ | C2 | C3 | C4 | (C %) |
| 442 | 74 | 11 | 36 | 20 | 44 | 36 | 26 | 79 | 47 | 14 |

Example 6—Conversion of $CO_2$ to Olefins

To determine the performance of the catalyst in the conversion of $CO_2$ to olefins, the FeNa catalyst was prepared and calcined according to the methods described herein. The calcined FeNa catalyst was subsequently washed with DI water and pelletized at 40 kN. The pellet was sieved to obtain particles of 250-500 μm. Subsequently, 1 g of the FeNa catalyst was loaded to a fixed bed reactor for testing after mixing with silicon carbide at a volume ratio=1:1. Reduction was carried out at 580° C. for 6 hours in $H_2$ and ambient pressure at a space velocity of 2000 ml/(g·h). Activation was carried out at 300° C. for 4 hours in CO and $H_2$ with $H_2/CO$ ratio=2 at 10 barg and a space velocity of 2000 ml/(g·h). The $CO_2$ reaction was carried out at 350° C. in $CO_2$ and $H_2$ with $H_2/CO_2$ ratio=3 at 15 barg and a space velocity of 5500 ml/(g·h).

The catalytic performance of the FeNa catalyst for the conversion of $CO_2$ to olefins was monitored and the relevant experimental data is presented in Table 6.

TABLE 6

Performance of the FeNa catalyst for $CO_2$ to olefins reaction, with $X(CO_2)$ the conversion of $CO_2$, $S(CH_4)$ and S(CO) are the selectivity towards $CH_4$ and CO respectively

| | $X(CO_2)$ | $S(CH_4)$ | S(CO) | | % of Olefins [mol C %] | | | | Hydrocarbon distribution [mol C %] | | |
|---|---|---|---|---|---|---|---|---|---|---|---|
| TOS (h) | mol C % | mol C % | mol C % | LO Yield | C2 | C3 | C4 | C2-C4 | $CH_4$ | C2-C4 | C5+ |
| 2 | 42 | 11 | 14 | 9.1 | 79 | 89 | 84 | 84.5 | 13 | 30 | 57 |
| 4 | 44 | 12 | 13 | 10.0 | 79 | 90 | 83 | 84.6 | 14 | 30 | 56 |
| 6 | 44 | 13 | 12 | 10.2 | 80 | 90 | 84 | 85.0 | 14 | 31 | 55 |
| 8 | 44 | 13 | 12 | 9.9 | 80 | 90 | 85 | 85.5 | 13.8 | 29.7 | 56.5 |
| 10 | 45 | 13 | 12 | 10.2 | 80 | 91 | 85 | 85.8 | 14.1 | 30.0 | 55.9 |
| 18 | 45 | 13 | 11 | 10.2 | 81 | 91 | 86 | 86.6 | 13.8 | 29.3 | 56.8 |
| 20.0 | 46 | 13 | 11 | 10.4 | 81 | 91 | 88 | 87.4 | 14.0 | 29.4 | 56.6 |
| 22.0 | 46 | 13 | 11 | 10.6 | 82 | 91 | 85 | 86.5 | 14.2 | 30.2 | 55.6 |
| 26.0 | 46 | 13 | 11 | 10.8 | 82 | 91 | 85 | 86.5 | 14.1 | 30.6 | 55.3 |

The results in Table 6 demonstrate that the FeNa catalyst prepared by the methods described herein can achieve a light olefin yield of 10.8% at a 002 conversion of 46% with very high percentage of olefin in 02-04 and relatively low $CH_4$ and 00 selectivity. Following these preliminary results, further optimization to improve the olefin yield may be performed.

Example 7. Effect of Br Content on Catalyst Performance

To investigate the effect of bromine in the catalyst on the conversion of carbon dioxide; a batch of unwashed FeNa catalyst prepared by the methods described herein was tested first in CO Fischer Tropsch Olefin production until high conversion of CO was achieved. The catalyst was subsequently tested for the Fischer Tropsch conversion of $CO_2$. The results are provided below in Table 7.

Further, the method of preparing a Na-promoted iron described herein can be conveniently scaled up for preparation of the selective FeNa catalyst at an industrial scale.

TABLE 7

Performance of FeNa catalyst for CO and $CO_2$ Fischer Tropsch conversion.
Reduction: 600 °C, 2 h 0 barg, SV = 12000 ml/(gh)$^{-1}$
Activation: 290 °C, 24 h 10 barg. $H_2$/CO ratio = 1. SV = 2000 ml/(gh)$^{-1}$
Reaction(CO): 370 °C 20 barg. $H_2/CO_2$ = 1. SV = 2000 ml/(gh)$^{-1}$ 24 h
370 °C 20 barg. $H_2/CO_2$ = 2. SV = 2000 ml/(gh)$^{-1}$ 6 h
Reaction($CO_2$): 350 °C 15 barg. $H_2/CO_2$ = 3.
SV = 5500 ml/(gh)$^{-1}$

| GC | TOS | X(CO) mol | S(CH4) mol | S(CO2) mol | LO Yield | OP ratio | | | | Hydrocarbon distribution | | | |
|---|---|---|---|---|---|---|---|---|---|---|---|---|---|
| run | (hrs) | C % | C % | C % | (GC) | C2 | C3 | C4 | C2-C4 | CH4 | C2-C4 | C5+ | $H_2$/CO |
| 22 | 20 | 95 | 6 | 31 | 19.0 | 61 | 88 | 82 | 77.8 | 17 | 37 | 46 | 1 |
| 25 | 26 | 97.0 | 9 | 21 | 21 | 58 | 85 | 81 | 76.0 | 8 | 36 | 46 | 2 |

| GC | TOS | X(CO2) mol | S(CH4) mol | S(CO) mol | LO Yield | OP ratio | | | | Hydrocarbon distribution | | |
|---|---|---|---|---|---|---|---|---|---|---|---|---|
| run | (hrs) | C % | C % | C % | (GC) | C2 | C3 | C4 | C2-C4 | CH4 | C2-C4 | C5+ |
| 49 | 70.4 | 39 | 12 | 25 | 11.2 | 78 | 91 | 88 | 86.0 | 18.8 | 44.3 | 36.9 |

It was found that the unwashed FeNa catalyst can achieve a light olefin yield of 11.2% after full activation with CO. The FeNa catalyst has a $CO_2$ conversion of 39% with very high percentage of olefin in $C_2$-$C_4$ and maintained low $CH_4$, but with slightly higher CO selectivity.

The result obtained by using the calcined, but unwashed FeNa catalyst for the conversion of CO followed by $CO_2$ is similar to that of Example 6 which utilizes a calcined catalyst which is washed. It is believed that washing FeNa after calcination will help to remove excess Br. During CO reaction, water as the by-product from the reaction will also remove excess Br.

The similar result obtained above indicates that Br may be leeched by water which is formed as a by-product during the CO Fischer Tropsch reaction. This also suggests that Br plays a role during the initial activation of the catalyst but may not be required after the catalyst reaches steady state. From Table 7, LO yield was lower under $CO_2$ flow, however considering the much lower conversion (39% $CO_2$ conversion vs. 97% CO conversion), the FeNa catalyst is actually more selective to light olefins under $CO_2$. Therefore by activation of unwashed FeNa catalyst via the CO reaction, the catalyst achieved good performance.

INDUSTRIAL APPLICABILITY

The method as described herein allows for a one-pot synthesis of a sodium-promoted nano-sized, iron-based catalyst which may be used in a Fisher-Tropsch process. In particular, the iron catalyst prepared by the method described herein can be used for the selective conversion of carbon monoxide and carbon dioxide to light olefins, with minimal hydrogenation to methane. Light olefins produced from the Fischer Tropsch reaction catalyzed by the Iron-sodium nano-sized catalyst prepared herein may subsequently be used as fuels and lubrication oils.

The invention claimed is:

1. A method of preparing a nano-sized, iron-based catalyst, the method comprising:

i) mixing a solution containing an iron salt with a surfactant to form a mixture;

ii) adding a basic salt solution comprising a salt of alkali metals to the mixture to form a precipitate; and iii) without washing said precipitate, collecting said precipitate, immediately followed by drying the precipitate in air before calcining said precipitate to form the iron-based catalyst, said iron-based catalyst at least partially comprising said alkali metal of said basic salt and adopts an iron-based spinel crystalline phase without hematite or magnetite phase.

2. The method of claim 1, wherein the basic salt solution comprises hydroxide, carbonate, or bicarbonate anions.

3. The method of claim 2, wherein the basic salt is sodium hydroxide, lithium hydroxide, potassium hydroxide, cesium hydroxide, or combinations thereof.

4. The method of claim 1, wherein the adding step comprises providing a molar ratio of elemental iron to the alkali metal of the basic salt of from 1:2 to 1:10.

5. The method of claim 1, wherein the solution of step i) comprises at least one or more additional salts of (a) a transition metal independently selected from groups 3 to 7 and 9 to 11 of the Periodic Table of Elements, (b) Mg, (c) Ca, (d) Li, and (e) K.

6. The method of claim 5, wherein the transition metal is Ni, Mn, La, Co, Ce, or a combination thereof, or wherein the transition metal salt comprises an anion selected from the group consisting of hydroxide, carbonate, bicarbonate, nitrate, nitrite, chloride, fluoride, bromide, iodide, phosphate, pyrophosphate, perchlorate, and mixtures thereof.

7. The method of claim 5, wherein the solution of step i) comprises a molar ratio of elemental transition metal to iron of from 1:8 to 1:100.

8. The method of claim 1, wherein the adding step ii) further comprises introducing a silicate to the mixture and precipitating said iron-based catalyst in the presence of the silicate to thereby form a silicate-supported iron-based catalyst.

9. The method of claim 8, wherein the silicate comprises one or more alkoxy groups of 2 to 5 carbon atoms.

10. The method of claim 8, wherein the adding step comprises providing a molar ratio of elemental iron to said silicate of from 1:5 to 1:15.

11. The method of claim 1, wherein the iron salt is an iron (II) or iron (III) salt, or wherein the iron salt comprises an anion selected from the group consisting of nitrate, chloride, fluoride, bromide, iodide, phosphate, pyrophosphate and perchlorate.

12. The method of claim 1, wherein the surfactant is an ionic surfactant.

13. The method of claim 1, wherein the molar ratio of iron to the surfactant is 1:0.5 to 1:2, or wherein the calcining step is carried out at a temperature of 400° C. to 600° C. for 1 hour to 3 hours.

14. The method of claim 1, wherein the surfactant comprises a halide anion.

* * * * *